United States Patent
Govari

(10) Patent No.: US 12,102,381 B2
(45) Date of Patent: Oct. 1, 2024

(54) FOCAL ABLATION CATHETER INCORPORATING A GUIDEWIRE INSERTED THROUGH IRRIGATION CHANNEL

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 118 days.

(21) Appl. No.: 17/187,546

(22) Filed: Feb. 26, 2021

(65) Prior Publication Data

US 2022/0273362 A1 Sep. 1, 2022

(51) Int. Cl.
*A61B 18/14* (2006.01)
*A61B 18/00* (2006.01)

(52) U.S. Cl.
CPC .............. *A61B 18/1492* (2013.01); *A61B 2018/00351* (2013.01); *A61B 2018/00577* (2013.01); *A61B 2018/00779* (2013.01); *A61B 2218/002* (2013.01)

(58) Field of Classification Search
CPC ...... A61B 18/1492; A61B 2018/00351; A61B 2018/00577; A61B 2018/00779; A61B 2218/002
See application file for complete search history.

(56) References Cited

U.S. PATENT DOCUMENTS

| 5,391,199 | A | | 2/1995 | Ben-Haim | |
| 5,895,355 | A | * | 4/1999 | Schaer | A61B 5/6853 |
| | | | | | 606/41 |
| 6,239,724 | B1 | | 5/2001 | Doron et al. | |
| 6,332,089 | B1 | | 12/2001 | Acker et al. | |
| 6,484,118 | B1 | | 11/2002 | Govari | |
| 6,618,612 | B1 | | 9/2003 | Acker et al. | |
| 6,690,963 | B2 | | 2/2004 | Ben-Haim et al. | |
| 9,855,094 | B2 | * | 1/2018 | Christian | A61B 18/1492 |
| 2002/0065455 | A1 | | 5/2002 | Ben-Haim et al. | |
| 2003/0093104 | A1 | * | 5/2003 | Bonner | A61B 17/3478 |
| | | | | | 606/185 |

(Continued)

FOREIGN PATENT DOCUMENTS

WO 9605768 A1 2/1996

OTHER PUBLICATIONS

Extended European Search Report dated Jul. 13, 2022, from corresponding Appl. No. 22158765.2.

*Primary Examiner* — Linda C Dvorak
*Assistant Examiner* — Abigail Bock
(74) *Attorney, Agent, or Firm* — Troutman Pepper Hamilton Sanders LLP

(57) ABSTRACT

A catheter includes an ablation electrode and an irrigation channel. The ablation electrode is configured to ablate tissue of a patient organ and is fitted over an insertion tube for insertion into the patient organ. The irrigation channel includes: (i) a lumen which is formed along an axis of the insertion tube, and is configured to flow irrigation fluid to the ablation electrode, and (ii) one or more irrigation holes, which are formed in the ablation electrode, and are configured to apply the irrigation fluid to the organ. The irrigation channel is configured to simultaneously (i) receive a guidewire for guiding the catheter and (ii) flow the irrigation fluid.

13 Claims, 3 Drawing Sheets

(56) References Cited

U.S. PATENT DOCUMENTS

| | | |
|---|---|---|
| 2003/0120150 A1 | 6/2003 | Govari |
| 2004/0068178 A1 | 4/2004 | Govari |
| 2008/0108946 A1 | 5/2008 | Nash et al. |
| 2008/0243214 A1* | 10/2008 | Koblish .................. A61N 1/05 606/41 |
| 2013/0267901 A1 | 10/2013 | Bellisario et al. |
| 2013/0310823 A1 | 11/2013 | Gelfand et al. |
| 2014/0163480 A1 | 6/2014 | Govari et al. |

* cited by examiner

FOCAL ABLATION CATHETER INCORPORATING A GUIDEWIRE INSERTED THROUGH IRRIGATION CHANNEL

FIELD OF THE INVENTION

The present invention relates generally to medical catheters, and particularly to methods and systems for maneuvering a focal ablation catheter using a guidewire.

BACKGROUND OF THE INVENTION

Focal catheters may be used in various medical applications, such as in cardiology. Several techniques for maneuvering focal catheters using a guidewire have been published.

For example, U.S. Patent Application Publication 2013/0267901 describes a catheterization system that includes a catheter including a body with proximal and distal ends and defining first and second lumens extending therethrough, and a stylet. The stylet includes first and second stylet portions each having proximal and distal end regions, wherein the distal end regions of the first and second stylet portions together define a tapered penetrating portion. The first and second stylet portions are configured and dimensioned to be slidably positioned within the first and second lumens of the catheter, respectively. The first and second stylet portions extend from the proximal end of the catheter and beyond the distal end of the catheter, and are independently movable in relation to each other to facilitate selective removal of the first stylet portion and/or the second stylet portion from the catheter.

U.S. Patent Application Publication 2008/0108946 describes an intra-luminal device for the extraction of occlusive or partially occlusive material. The device comprises a novel catheter extension which minimizes cavitation of extracted fluids and also allows the better navigation of tortuous lumens or vasculature.

SUMMARY OF THE INVENTION

An embodiment of the present invention that is described herein provides a catheter, including an ablation electrode and an irrigation channel. The ablation electrode is configured to ablate tissue of a patient organ and is fitted over an insertion tube for insertion into the patient organ. The irrigation channel includes: (i) a lumen which is formed along an axis of the insertion tube, and is configured to flow irrigation fluid to the ablation electrode, and (ii) one or more irrigation holes, which are formed in the ablation electrode, and are configured to apply the irrigation fluid to the organ, the irrigation channel is configured to simultaneously (i) receive a guidewire for guiding the catheter and (ii) flow the irrigation fluid.

In some embodiments, the ablation electrode has an opening for traversing the guidewire therethrough. In other embodiments, the opening and the guidewire have matching diameters, so as to prevent leakage of the irrigation fluid through the opening. In yet other embodiments, the catheter further includes one or more sensing electrodes, which are disposed on the insertion tube and, when placed in contact with tissue of the organ, are configured to sense electrical signals from the tissue.

There is additionally provided, in accordance with an embodiment of the present invention, a method including inserting a guidewire into a patient organ, and positioning a distal tip of the guidewire at an ablation site. A proximal tip of the guidewire is inserted through an irrigation channel of a catheter, the irrigation channel includes: (i) a lumen which is formed along an axis of an insertion tube of the catheter for flowing irrigation fluid to an ablation electrode fitted on the insertion tube and for traversing the guidewire through the ablation electrode, and (ii) one or more irrigation holes, formed in the ablation electrode for applying the irrigation fluid to the organ. The catheter is slided along the guidewire and positioned at the ablation site. The irrigation fluid is applied, through the one or more irrigation holes, to the organ while the guidewire resides within the irrigation channel.

There is further provided, in accordance with an embodiment of the present invention, a method for producing a catheter for ablating tissue, the method includes fitting, over an insertion tube for insertion into a patient organ, an ablation electrode for ablating the tissue. An irrigation channel is produced in the ablation electrode, by: ((i) forming, along an axis of the ablation electrode, a lumen for flowing irrigation fluid to the ablation electrode, and for inserting a guidewire therethrough, and (ii) forming, in the ablation electrode, one or more irrigation holes for applying the irrigation fluid to the organ.

There is further provided, in accordance with an embodiment of the present invention, a catheter including an insertion tube for insertion into a patient organ, and an irrigation channel. The irrigation channel includes: (i) a lumen which is formed along an axis of the insertion tube, and is configured to flow irrigation fluid to a distal end of the insertion tube, and (ii) one or more irrigation holes, which are formed in the distal end of the insertion tube, and are configured to apply the irrigation fluid to the organ. The irrigation channel is configured to simultaneously (i) receive a guidewire for guiding the catheter and (ii) flow the irrigation fluid.

In some embodiments, the catheter further includes one or more: (i) ablation electrodes or (ii) sensing electrodes, which are disposed on the insertion tube and, when placed in contact with tissue of the organ, are configured for at least one of: (i) applying one or more ablation pulses to the tissue, and (ii) sensing one or more electrical signals from the tissue.

The present invention will be more fully understood from the following detailed description of the embodiments thereof, taken together with the drawings in which:

DETAILED DESCRIPTION OF EMBODIMENTS

Overview

Figure 1:
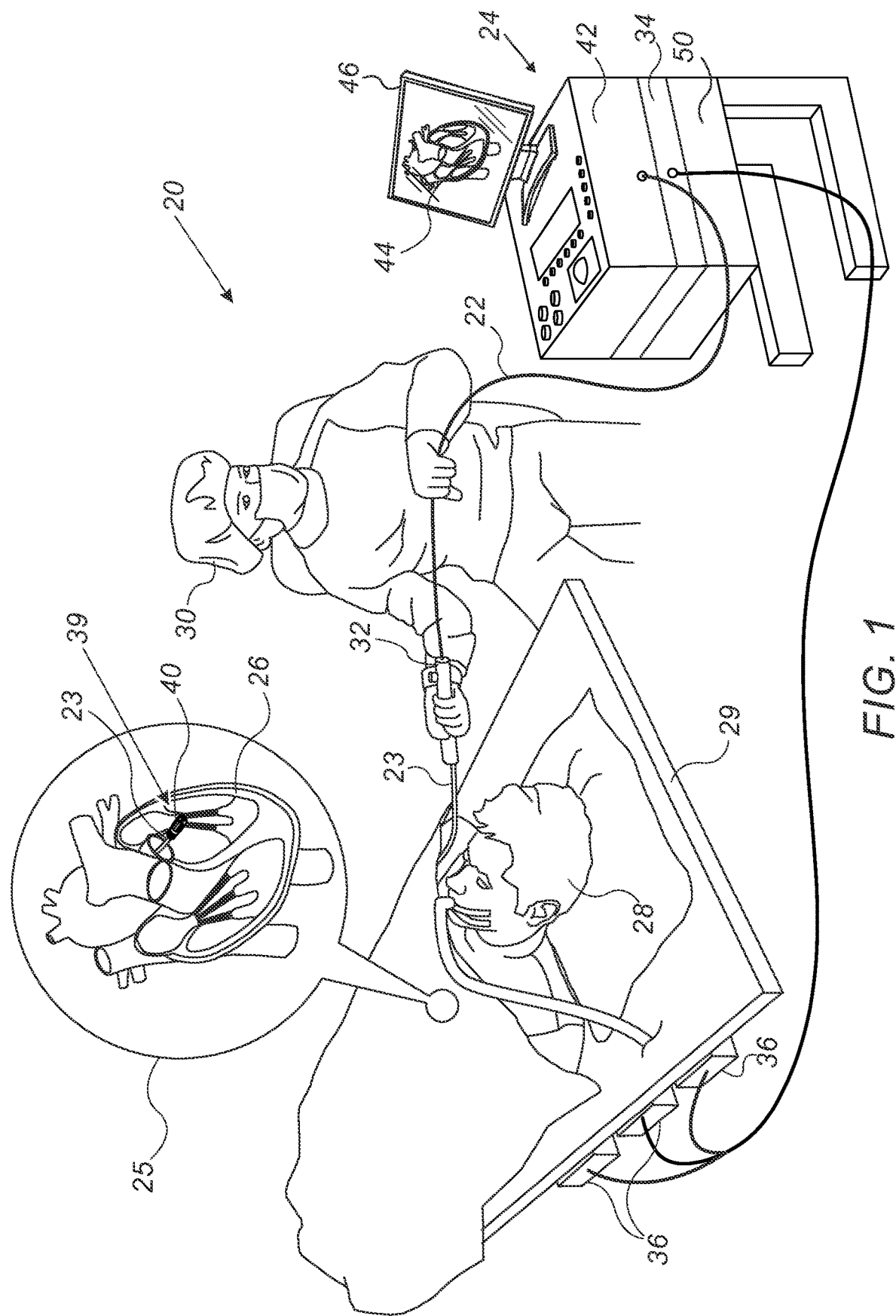
FIG. 1 is a schematic, pictorial illustration of a catheter-based position-tracking and ablation system, in accordance with an embodiment of the present invention.

In ablation procedures, such as radiofrequency (RF) ablation, physicians typically use catheters having ablation electrodes configured to ablate tissue at ablation site for treating arrhythmia in a patient organ, such as in a patient heart. In some cases, ablation has to be carried out at ablation sites that are difficult to reach with the catheter, and may also have a small area intended to be ablated, which further complicates the catheter maneuvering and the ablation process of the tissue.

Embodiments of the present invention that are described hereinbelow provide improved techniques for performing RF ablation in small and difficult-to-reach ablation sites. Such sites are also referred to herein as micro-ablation sites, and such procedures are also referred to herein as micro-ablation procedures.

In some embodiments, a catheter for performing a micro ablation procedure comprises an insertion tube for insertion into a patient organ, in the present example, patient heart. The catheter comprises ablation electrodes, which are disposed on the insertion tube, and when placed in contact with the tissue intended to be ablated (also referred to herein as target tissue), the ablation electrodes are configured for ablating the tissue at the ablation site.

During the tissue ablation, it is important to control the temperature profile of the ablated tissue, and the temperature of the ablation electrodes. In some embodiments, the catheter further comprises an irrigation channel, which is configured to apply irrigation fluid to the ablated tissue, and is controlled by a processor so as to maintain the temperature described above.

In some embodiments, the irrigation cannel comprises a lumen which is formed along a longitudinal axis of the insertion tube, and is configured to flow the irrigation fluid to the distal end of the insertion tube. The irrigation channel further comprises a manifold having multiple irrigation holes, which are formed in the distal end of the insertion tube, and are configured to apply the irrigation fluid to the tissue.

In some embodiments, the insertion tube has an opening, which is sized and shaped to be sealed by a guidewire traversing through the irrigation channel, so as to prevent leakage of the irrigation fluid through the opening. For example, the guidewire and the opening typically have matching diameters, so as to prevent the leakage.

In such embodiments, the irrigation channel is configured to simultaneously (i) receive a guidewire for guiding the catheter and (ii) flow and apply the irrigation fluid to the tissue being ablated.

In some embodiments, during the ablation procedure, the physician inserts and maneuvers the distal tip of the guidewire into the ablation site. After inserting the guidewire into the irrigation channel, the physician slides the distal end of the catheter along the guidewire, so as to position the catheter distal end at the ablation site, and to place one or more of the ablation electrodes in contact with the tissue intended to be ablated.

The disclosed techniques improve the maneuverability of an ablation catheter without increasing the size of the catheter distal-end. Therefore, such catheters may be used to carry out RF ablation procedures at small and difficult-to-reach ablation sites. Moreover, the disclosed techniques reduce the cycle time of such ablation procedures, by allowing the physician to apply ablation pulses and irrigation fluid to the target tissue, as soon as the ablation electrodes are placed in contact with the target tissue, without the time-consuming process of retracting the guidewire.

System Description

FIG. 1 is a schematic, pictorial illustration of a catheter-based position-tracking and ablation system 20, in accordance with an embodiment of the present invention. In some embodiments, system 20 comprises a catheter 22, in the present example a cardiac catheter having a focal shape, and a control console 24. In the embodiment described herein, catheter 22 may be used for any suitable therapeutic and/or diagnostic purposes, such as ablation of tissue in a heart 26 and for mapping cardiac arrhythmias by sensing intra-cardiac electrical signals.

In some embodiments, console 24 comprises a processor 42, typically a general-purpose computer, with suitable front end and interface circuits for exchanging signals with catheter 22 (e.g., receiving intra-cardiac electrical signals and applying ablation pulses to tissue of heart 26), and for controlling other components of system 20 described herein. Processor 42 may be programmed in software to carry out the functions that are used by the system, and is configured to store data for the software in a memory 50. The software may be downloaded to console 24 in electronic form, over a network, for example, or it may be provided on non-transitory tangible media, such as optical, magnetic or electronic memory media. Alternatively, some or all of the functions of processor may be carried out using an application-specific integrated circuit (ASIC) or any suitable type of programmable digital hardware components.

Reference is now made to an inset 25. In some embodiments, catheter 22 comprises a distal-end assembly 40 having a focal shape (shown in detail in FIGS. 2 and 3 below), and a shaft 23 for inserting distal-end assembly 40 to a target location for ablating tissue in heart 26. During an ablation procedure, physician 30 inserts catheter 22 through the vasculature system of a patient 28 lying on a table 29. Physician 30 moves distal-end assembly 40 to the target location in heart 26 using a manipulator 32 near a proximal end of catheter 22, which is connected to interface circuitry of processor 42.

In some embodiments, catheter 22 comprises a position sensor 39 of a position tracking system, which is coupled to the distal end of catheter 22, e.g., in close proximity to distal-end assembly 40. In the present example, position sensor 39 comprises a magnetic position sensor, but in other embodiments, any other suitable type of position sensor (e.g., other than magnetic-based) may be used.

Reference is now made back to the general view of FIG. 1. In some embodiments, during the navigation of distal-end assembly 40 in heart 26, processor 42 receives signals from magnetic position sensor 39 in response to magnetic fields from external field generators 36, for example, for the purpose of measuring the position of distal-end assembly 40 in heart 26. In some embodiments, console 24 comprises a driver circuit 34, configured to drive magnetic field generators 36. Magnetic field generators 36 are placed at known positions external to patient 28, e.g., below table 29.

In some embodiments, processor 42 is configured to display, e.g., on a display 46 of console 24, the tracked position of distal-end assembly 40 overlaid on an image 44 of heart 26.

The method of position sensing using external magnetic fields is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Figure 2:
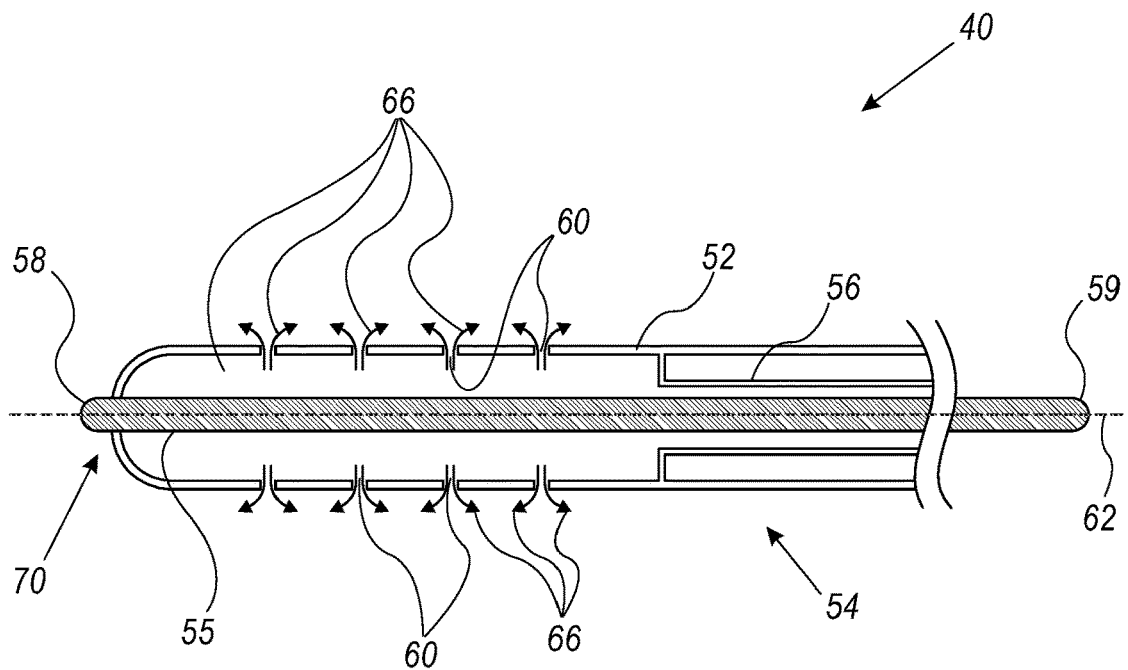
FIG. 2 is a schematic, sectional view of a distal-end assembly of a focal-shape ablation catheter, in accordance with an embodiment of the present invention.

Catheter Insertion Over a Guidewire Threaded Through the Catheter Irrigation Channel FIG. 2 is a schematic, sectional view of distal-end assembly 40, in accordance with an embodiment of the present invention.

In some embodiments, distal-end assembly 40 comprises an ablation electrode 52, which is configured to ablate tissue of patient heart 26, is fitted over a distal end of an insertion tube (shown in FIG. 3 below) for inserting catheter 22 into heart 26 to carry out the aforementioned cardiac ablation procedure. Distal-end assembly 40 further comprises an irrigation channel 54 having a lumen 56 and one or more irrigation holes 60.

In some embodiments, lumen 56 is formed along an axis 62 of insertion tube (not shown) and ablation electrode 52, and is configured to flow irrigation fluid 66 to ablation electrode 52.

In some embodiments, irrigation holes 60 are formed in ablation electrode 52, and are configured to apply irrigation fluid 66 to tissue of heart 26, typically, but not necessarily, during ablation of the tissue.

In some ablation procedures, the anatomical structure of heart 26 complicates the maneuvering of distal-end assembly 40 to an ablation site for applying the ablation pulses. In some embodiments, physician 30 may use a guidewire 55 for improving the maneuverability of distal-end assembly 40 in heart 26. Guidewire 55 is flexible and yet sufficiently stiff, has a small diameter, e.g., about 0.89 mm or any other suitable diameter, and configured to have improved maneuverability over that of catheter 22 and distal-end assembly 40.

In some embodiments, guidewire 55 may comprise any suitable type of guidewire, such as Amplatz guidewire, produced by Boston Scientific (Middlesex County, Marlborough, Massachusetts).

In the context of the present disclosure and in the claims, the terms "about" or "approximately" for any numerical values or ranges indicate a suitable dimensional tolerance that allows the part or collection of components to function for its intended purpose as described herein.

In some embodiments, ablation electrode 52 has an opening 70, which is sized and shaped to be sealed when guidewire 55 is threaded through irrigation channel 54, so as to prevent leakage of irrigation fluid 66 through opening 70. For example, opening 70 and guidewire 55 may have matching diameters, e.g., 0.89 mm, so as to prevent leakage of the irrigation fluid through the opening.

Additionally or alternatively, at least a sealing ring (not shown) may be fitted within opening 70. The sealing ring is configured to: (i) snugly fit over guidewire 55 when distal-end assembly 40 slides over guidewire 55, and (ii) prevent leakage of irrigation fluid 66 through opening 70 when applying irrigation fluid 66 through irrigation channel 54.

Note that in such embodiments, distal-end assembly 40 is configured to simultaneously: (i) receive guidewire 55 for guiding catheter 22 in heart 26, and (ii) flow irrigation fluid 66 through lumen 56 and irrigation holes 60, without leakage of irrigation fluid 66 through opening 70.

Figure 3:
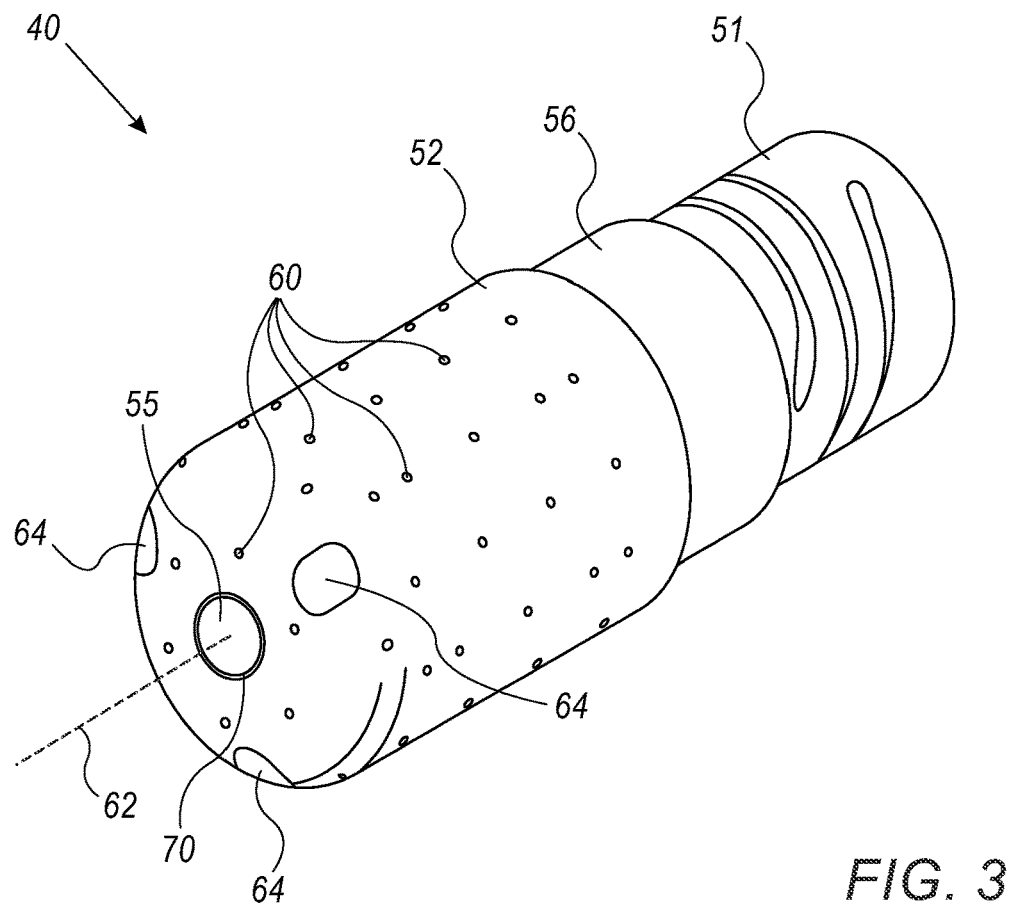
FIG. 3 is a schematic, pictorial illustration of a distal-end assembly of a focal-shape ablation catheter, in accordance with an embodiment of the present invention.

FIG. 3 is a schematic, pictorial illustration of distal-end assembly 40, in accordance with an embodiment of the present invention.

In some embodiments, distal-end assembly 40 comprises one or more sensing electrodes 64, which are coupled to an insertion tube 51, and are inserted into openings formed at suitable locations in ablation electrode 52. Sensing electrodes 64 are configured to sense electrical signals from tissue of heart 26, as described above.

In other embodiments, instead of ablation electrode 52, distal-end assembly 40 may comprise the aforementioned insertion tube or any other suitable component, so that at least one of electrodes 64 comprises an ablation electrode or a sensing electrode.

In yet other embodiments, distal-end assembly 40 may comprise, instead of at least one of sensing electrodes 64, one or more ablation electrodes, which are configured to apply ablation pulses to tissue of heart 26, as described above.

In the present example, distal-end assembly 40 comprises three sensing electrodes 64, which are disposed about axis 62 and are electrically insulated from ablation electrode 52. Each sensing electrode 64 is surrounded with irrigation holes 60 for controlling the temperature of ablation electrode 52, sensing electrodes 64, and the temperature profile in the ablated tissue.

In one implementation of the techniques described above, catheter 22 comprises a QDot Micro radiofrequency (RF) ablation catheter, produced by Biosense Webster Inc. (Irvine, Calif.), each sensing electrode 64 has a surface area of about 0.167 mm2, and the distance between adjacent sensing electrodes 64 is about 1.349 mm.

In some embodiments, a distal tip 58 of guidewire 55 is threaded along axis 62, through lumen 56 and opening 70, and maneuvered, through the vasculature of patient 28, to the ablation site by physician 30 or by any other suitable user of system 20. Subsequently, physician 30 slides distal-end assembly 40 along guidewire 55 to heart 26. In alternative embodiments, physician 30: (i) inserts distal tip 58 of guidewire 55 into patient 28 and maneuvers distal tip 58, through the vasculature of patient 28, to the ablation site in heart 26, and (ii) inserts a proximal tip 59 of guidewire 55 into lumen 56 of distal-end assembly 40, and slides distal-end assembly 40 along guidewire 55, to the ablation site in heart 26. Note that in both embodiments, when applying irrigation fluid 66 to the tissue of heart 26, guidewire 55 typically remains inserted through irrigation channel 54 of distal-end assembly 40 as shown and described in FIG. 2 above.

Note that the disclosed techniques improve the maneuverability of catheter 22 without increasing the size of catheter 22 or distal-end assembly 40, so that physician 30 may carry out RF ablation at small and difficult-to-reach ablation sites, also referred to herein as micro ablation.

Performing Micro-Ablation by Maneuvering Catheter Over Guidewire

Figure 4:
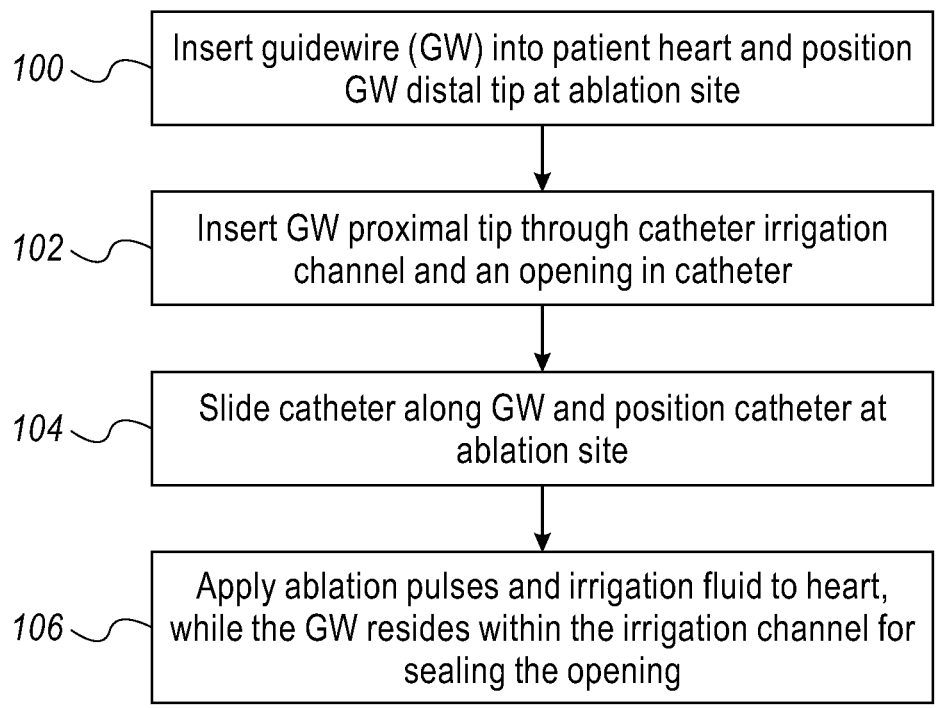
FIG. 4 is a flow chart that schematically illustrates a method for performing micro ablation by maneuvering a focal catheter using a guidewire, in accordance with an embodiment of the present invention.

FIG. 4 is a flow chart that schematically illustrates a method for performing micro-ablation by maneuvering catheter 22 over guidewire 55, in accordance with an embodiment of the present invention.

The method begins at a first guidewire insertion step 100, with guidewire 55 being inserted (e.g., by physician 30) into heart 26 and distal tip 58 of guidewire 55 is positioned, at ablation site within heart 26. At a second guidewire insertion step 102, proximal tip 59 of guidewire 55 is inserted through: (i) lumen 56 of irrigation channel 54, and (ii) opening 70 of catheter 22.

At a catheter positioning step 104, distal-end assembly 40 of catheter 22 is moved, by sliding along guidewire 55 toward distal tip 58, and positioned at the ablation site, as described in detail in FIGS. 2 and 3 above.

At an ablation step 106 that concludes the method, physician 30 controls catheter 22 (e.g., via processor 42) to apply to the ablation site in heart 26: (i) ablation pulses, using ablation electrodes 64, and (ii) irrigation fluid 66 via irrigation channel 54. Note that when applying irrigation fluid 66, guidewire 55 resides within irrigation channel 54 for sealing opening 70, and thereby, preventing leakage of irrigation fluid 66 through opening 70.

Producing Distal-End Assembly of Catheter for Performing Micro-Ablation

Figure 5:
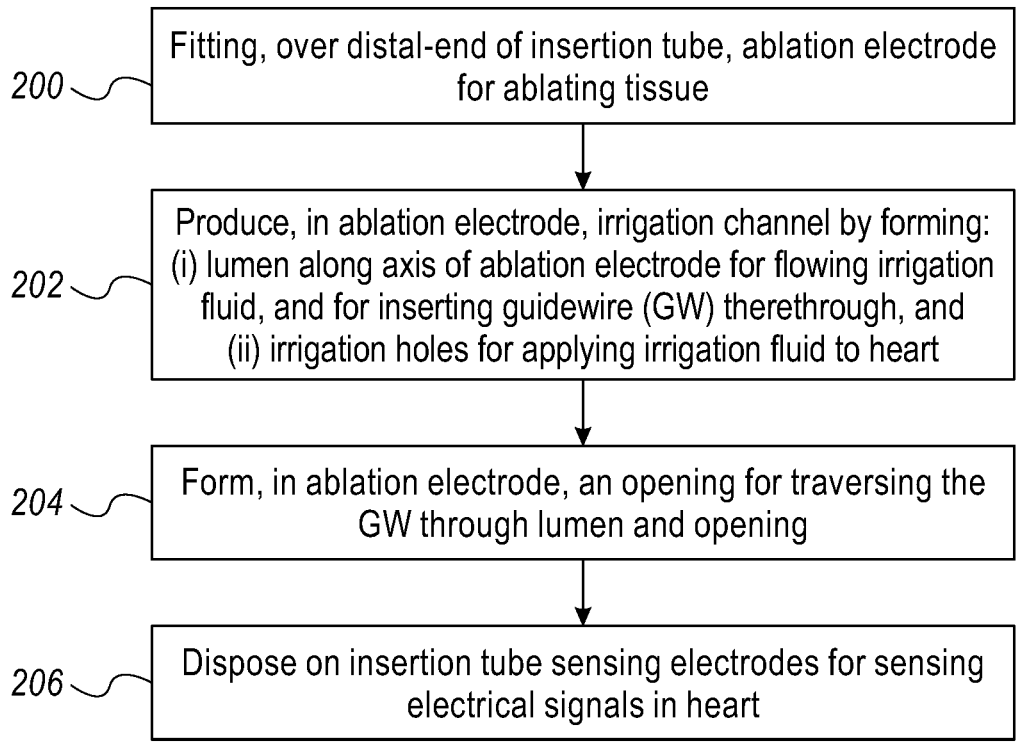
FIG. 5 is a flow chart that schematically illustrates a method for producing a catheter for ablating tissue, in accordance with an embodiment of the present invention.

FIG. 5 is a flow chart that schematically illustrates a method for producing distal-end assembly 40 of catheter 22, in accordance with an embodiment of the present invention.

The method begins at an ablation electrode fitting step 200, with fitting ablation electrode 52 for ablating tissue, over the distal end of insertion tube 51 for insertion into patient heart 26. At an irrigation channel forming step 202, irrigation channel 54 is produced within ablation electrode 52, by: (i) forming lumen 56 along axis 62 of ablation electrode 52 for flowing irrigation fluid toward ablation electrode 52, and for inserting guidewire 55 therethrough, and (ii) forming irrigation holes 60 for applying irrigation fluid 66, through ablation electrode 52, to heart 26 during the ablation procedure.

At an opening formation step 204, opening 70 is formed in ablation electrode 52, for traversing guidewire 55 through lumen 56 and opening 70. In some embodiments, opening 70 is sized and shaped to be sealed by guidewire 55, so as to prevent leakage of irrigation fluid 66 through opening 70 when irrigating the tissue of heart 26, as described in detail in FIGS. 2 and 3 above. For example, opening 70 and guidewire 55 may have matching diameters (e.g., of about 0.89 mm each), so as to prevent the leakage of irrigation fluid 66 through opening 70. Additionally or alternatively, distal-end assembly 40 may comprise a sealing ring fitted within opening 70 for preventing the leakage of irrigation fluid 66 through opening 70.

At a sensing electrode disposing step 206, which concludes the method, one or more sensing electrodes 64 are coupled to or disposed on insertion tube 51 and are threaded through opening in ablation electrode 52 for sensing electrical signals from the tissue of heart 26.

Although the embodiments described herein mainly address RF ablation procedures carried out at small and difficult-to-reach ablation sites, the methods and systems described herein can also be used in other applications, such as in ablation techniques other than RF-based, in electroporation and electrosurgical procedures, and in any sort of fluid delivery to small and/or difficult-to-reach sites in patient body, such as in accurate delivery of drugs.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A catheter comprising:
   an ablation electrode comprising a distal opening for traversing a guidewire therethrough, the ablation electrode configured to ablate tissue of a patient organ and fitted over an insertion tube for insertion into the patient organ;
   a sensing electrode, disposed at least partially in openings formed in the ablation electrode, the sensing electrode being disposed at least partially along a hemispherical portion of the ablation electrode and at least partially along a cylindrical portion of the ablation electrode such that, when placed in contact with tissue of the organ, the sensing electrode is configured to sense electrical signals from the tissue; and
   an irrigation channel, comprising: (i) a lumen which is formed along an axis of the insertion tube, and is configured to flow irrigation fluid to the ablation electrode, and (ii) one or more irrigation holes, which are formed in the ablation electrode, and are configured to apply the irrigation fluid to the organ, the ablation electrode, and the sensing electrode, wherein the irrigation channel is configured to simultaneously (i) receive the guidewire for guiding the catheter and (ii) flow the irrigation fluid.

2. The catheter according to claim 1, wherein the distal opening and the guidewire have matching diameters, so as to prevent leakage of the irrigation fluid through the distal opening.

3. The catheter according to claim 1, further comprising a processor configured to maintain a temperature of the ablation electrode and a temperature profile of the ablated tissue by controlling delivery of the irrigation fluid.

4. The catheter according to claim 1, further comprising a position sensor coupled to the distal end of the catheter.

5. A method, comprising:
   inserting a guidewire into a patient organ, and positioning a distal tip of the guidewire at an ablation site;
   inserting a proximal tip of the guidewire through an irrigation channel of a catheter, a distal tip of the catheter comprising an ablation electrode comprising a distal opening for traversing the guidewire therethrough and fitted on an insertion tube and a sensing electrode disposed at least partially in openings defined by the ablation electrode, the sensing electrode being disposed at least partially along a hemispherical portion of the ablation electrode and at least partially along a cylindrical portion of the ablation electrode and configured to sense electrical signals from tissue, the irrigation channel comprising: (i) a lumen which is formed along an axis of the insertion tube of the catheter for flowing irrigation fluid to the ablation electrode and for traversing the guidewire through the ablation electrode, and (ii) one or more irrigation holes, formed in the ablation electrode for applying the irrigation fluid to the organ, the ablation electrode, and the sensing electrode;
   sliding the catheter along the guidewire and positioning the catheter at the ablation site; and applying the irrigation fluid, through the one or more irrigation holes, to the organ, the ablation electrode, and the sensing electrode while the guidewire resides within the irrigation channel.

6. The method according to claim 5, wherein inserting the proximal tip comprises traversing the guidewire through: (i) the lumen, and (ii) an opening in the ablation electrode.

7. The method according to claim 6, wherein the opening and the guidewire have matching diameters, so as to prevent leakage of the irrigation fluid through the opening.

8. The method according to claim 5, further comprising sensing one or more electrical signals from the tissue of the organ.

9. A method for producing a catheter for ablating tissue, the method comprising:
fitting, over an insertion tube for insertion into a patient organ, an ablation electrode for ablating the tissue;
producing an irrigation channel in the ablation electrode, by: (i) forming, along an axis of the ablation electrode, a lumen for flowing irrigation fluid to the ablation electrode, and for inserting a guidewire therethrough, and (ii) forming, in the ablation electrode, one or more irrigation holes for applying the irrigation fluid to the organ, the ablation electrode, and a sensing electrode disposed at least partially in openings formed in the ablation electrode, the sensing electrode being disposed at least partially along a hemispherical portion of the ablation electrode and at least partially along a cylindrical portion of the ablation electrode and configured to sense electrical signals from tissue; and
producing, in the ablation electrode, a distal opening for traversing the guidewire through the lumen and the distal opening.

10. The method according to claim 9, wherein producing the opening comprises forming the opening, which is sized and shaped to be sealed by the guidewire for preventing leakage of the irrigation fluid through the opening.

11. The method according to claim 9, further comprising, disposing on the ablation electrode, one or more sensing electrodes for sensing electrical signals from the tissue.

12. A catheter, comprising:
an insertion tube for insertion into a patient organ, the insertion tube comprising a distal opening for traversing a guidewire therethrough;
an ablation electrode fitted on the insertion tube;
a sensing electrode disposed at least partially in openings defined by the ablation electrode, the sensing electrode being disposed at least partially along a hemispherical portion of the ablation electrode and at least partially along a cylindrical portion of the ablation electrode and configured to sense electrical signals from tissue; and
an irrigation channel, comprising: (i) a lumen which is formed along an axis of the insertion tube, and is configured to flow irrigation fluid to a distal end of the insertion tube, and (ii) one or more irrigation holes, which are formed in the distal end of the insertion tube, and are configured to apply the irrigation fluid to the organ, the ablation electrode, and the sensing electrode, wherein the irrigation channel is configured to simultaneously (i) receive the guidewire for guiding the catheter and (ii) flow the irrigation fluid.

13. The catheter according to claim 12, wherein the opening and the guidewire have matching diameters, so as to prevent leakage of the irrigation fluid through the opening.

* * * * *